(12) United States Patent
Cinti et al.

(10) Patent No.: US 7,357,914 B2
(45) Date of Patent: Apr. 15, 2008

(54) USE OF METAL CHELATES IN HUMAN OR ANIMAL FEEDING

(75) Inventors: Enrico Cinti, Piacenza (IT); Antonio Ciribolla, Reggio Emilia (IT)

(73) Assignee: Agristudio S.R.L., Reggio Emilia (IT)

( * ) Notice: Subject to any disclaimer, the term of this patent is extended or adjusted under 35 U.S.C. 154(b) by 0 days.

(21) Appl. No.: 10/526,737

(22) PCT Filed: Jun. 27, 2003

(86) PCT No.: PCT/IT03/00400

§ 371 (c)(1),
(2), (4) Date: Mar. 4, 2005

(87) PCT Pub. No.: WO2004/021802

PCT Pub. Date: Mar. 18, 2004

(65) Prior Publication Data
US 2005/0255146 A1    Nov. 17, 2005

(30) Foreign Application Priority Data
Sep. 6, 2002   (IT) ............................ RE2002A0067
Apr. 29, 2003  (IT) ............................ MI2003A0863

(51) Int. Cl.
*A61K 51/00* (2006.01)
*A61K 39/00* (2006.01)
*A61K 39/385* (2006.01)

(52) U.S. Cl. ............... 424/1.53; 424/179.1; 424/193.1; 514/836

(58) Field of Classification Search ............... 556/50; 514/6
See application file for complete search history.

(56) References Cited

U.S. PATENT DOCUMENTS

| | | | | |
|---|---|---|---|---|
| 2,745,745 A | | 5/1956 | Blake et al. | |
| 2,927,859 A | * | 3/1960 | Gordon | 424/705 |
| 3,035,920 A | * | 5/1962 | Knodt | 426/74 |
| 4,020,158 A | * | 4/1977 | Ashmead et al. | 514/6 |
| 4,855,495 A | * | 8/1989 | Takano | 562/581 |
| 5,583,243 A | | 12/1996 | Abdel-Monem | |
| 5,973,200 A | * | 10/1999 | Koenig | 562/581 |
| 6,403,143 B1 | | 6/2002 | Bevans et al. | |
| 6,458,981 B1 | * | 10/2002 | Ashmead et al. | 556/50 |
| 6,461,664 B1 | | 10/2002 | Ciribolla | |

FOREIGN PATENT DOCUMENTS

| | | |
|---|---|---|
| CN | 1 290 488 | 4/2001 |
| EP | 0133796 A1 * | 3/1985 |
| GB | 1 575 577 | 9/1980 |
| WO | 00/53032 A | 9/2000 |
| WO | WO 00/53032 A1 * | 9/2000 |
| WO | 02/30216 A | 4/2002 |

* cited by examiner

*Primary Examiner*—S. Tran
(74) *Attorney, Agent, or Firm*—Pearne & Gordon LLP (57) ABSTRACT

The present invention relates to the use in human and animal nutrition (monogastric and polygastric animals) of known chelates of bivalent metal Mg, Ca, Mn, Co, Cu, Zn and Fe with methionine hydroxy analogue. The present invention further relates to a method for preparing new chelates with methionine hydroxy analogue, both in solid form with iron (II), vanadium (iV) and (V) and molybdenum (V) and (VI), and in liquid form in aqueous solution with iron (II) and (III) and chrome (III). Eventually, the present invention relates to the use of said new chelates, both in solid form with iron (II), vanadium (IV) and (V) and molybdenum (V) and (VI), and in liquid form in aqueous solution with iron (II) and (III) and chrome (III), in human and animal nutrition.

5 Claims, 5 Drawing Sheets

USE OF METAL CHELATES IN HUMAN OR ANIMAL FEEDING

The present invention relates to the use in human and animal nutrition (monogastric and polygastric animals) of known chelates of bivalent metals Mg, Ca, Mn, Co, Cu, Zn and Fe with methionine hydroxy analogue. The present invention further relates to a method for preparing new chelates with methionine hydroxy analogue, both in solid form with iron (II), vanadium (IV) and (V) and molybdenum (V) and (VI), and in liquid form in aqueous solution with iron (II) and (III) and chrome (III). Eventually, the present invention relates to the use of said new chelates, both in solid form with iron (II), vanadium (IV) and (V) and molybdenum (V) and (VI), and in liquid form in aqueous solution with iron (II) and (III) and chrome (III), in human and animal nutrition.

It is known that a metal chelate is a compound originating from an organic molecule (such as an amino acid or a peptide chain or an alpha-keto acid or an alpha-hydroxy acid) and a metal ion through strong coordination bonds. Some known metal chelates are used in the field of human nutrition. Their use is due to the biological action performed by the metal element involved, as activator in several enzymatic reactions, and as regulator in various metabolic functions in all living organisms. The presence of a chelating molecule promotes the absorption, availability and use of the metal element since the latter is carried by the organic component in all areas of the organism. This results also in a strong reduction of losses of unused metals in dejections, and therefore in a significant economic saving and in an environmental advantage.

The general features that should characterize a highly bioavailable metal chelate are: (a) neutrality of complex (the positive charge of metal is balanced by the negative charge of ligands; (b) absence of negative counter-ions (chlorides, sulfates); (c) low molecular weight of complex (<1,500 Daltons); (d) well defined metal/chelating agent (bidentate) ratio, possibly $\leq 1:2$.

Moreover, metal chelates should be obtained from simple and clean processes with high yields starting from raw materials that can be easily found. These features can be implemented by means of suitable ligands, which should be easy to deproton and have at least two donor atoms in such a position to carry out chelation. Examples of ligands are amino acids and other organic acids suitably functionalized.

As far as iron is concerned, its administration in chelated form is particularly efficient against anemia. Anemia is a pathologic status of blood due to the reduction of the number of red blood cells, to the decrease of the amount of hemoglobin or to both deficiencies. Iron is fundamental for hemoglobin since it is the center in which oxygen is fixed into heme. Classes of people who need a higher amount of iron are menstruated or pregnant women, children under two years of age, vegetarians, people suffering from hemorrhoids, people suffering from ulcers and eventually blood donors. Symptoms felt by an anemic person are weariness, a higher sensibility to cold, irritableness, loss of concentration and heart palpitations.

Furthermore, iron can protect from viral or bacterial infections since it promotes the stimulation of the immune system. In addition, iron promotes the metabolism of vitamins belonging to B group.

It is known that the lack of these vitamins can result in diseases such as dermatitis or even more serious diseases such as pellagra (due to the deficiency of vitamin $B_3$). Iron intervenes in processes of synthesis of adrenaline and noradrenaline. Eventually, the lack of iron leads to a slow cicatrisation of wounds.

A first aim of the present invention is to suggest an integrator for administration in human nutrition. Said integrator is also administered to patients suffering from a deficiency of metal oligoelements such as: Mg, Ca, Mn, Co, Cu, Zn and Fe.

A second aim of the present invention is to suggest an integrator for agro-zootechnical nutrition to be administered to monogastric or polygastric animals. Said integrator is also administered to monogastric or polygastric animals needing an administration of metal oligoelements such as: Mg, Ca, Mn, Co, Cu, Zn and Fe with a higher bioavailability.

A third aim of the present invention is to suggest a method for preparing metal chelates with methionine hydroxy analogue or one of its salts, both in solid form with iron (II), vanadium (IV) and/or vanadium (V) and molybdenum (V) and/or molybdenum (VI), and in liquid form in aqueous solution with iron (II) and (III) and chrome (III), in which said metals are bonded to a bifunctional organic ligand with a strong coordination bond so as to form a stable metal chelate.

A further aim of the present invention is to suggest the use of said new chelates, both in solid form with iron (II), vanadium (IV) and/or vanadium (V) and molybdenum (V) and/or molybdenum (VI), and in liquid form in aqueous solution with iron (II) and (III) and chrome (III), for preparing metal integrators for human and animal nutrition.

In an embodiment of the present invention said first and second aim are achieved by suggesting the use of metal chelates [2:1] having the general formula (I):

$$(CH_3SCH_2CH_2CH(OH)COO)_2M.nH_2O \qquad (I)$$

in which the bifunctional chelating agent is 2-hydroxy-4-methylthiobutanoic acid, an alpha-hydroxy acid, known as "methionine hydroxy analogue" (MHA); M is a bivalent metal cation chosen from the group comprising: Co, Ca, Mg, Zn, Fe, Cu and Mn, and n is the number of water molecules; for preparing metal integrators for treating patients suffering from a deficiency of metal oligoelements or for administration in the agro-zootechnical field to monogastric or polygastric animals. In formula (I) there are zero to twelve water molecules, preferably zero to six. For instance, zero to four. 2-hydroxy-4-methylthiobutanoic acid builds with iron ion a chelate having a well defined stoichiometry, containing two molecules of chelating agent pro iron atom, in the same way as it builds chelates with bivalent metals Mg, Ca, Mn, Co, Cu and Zn.

The method for preparing metal chelates having formula (I) was described in international patent application PCT/IT99/00225, and consists in the direct reaction of MHA with the corresponding carbonates of bivalent metals Mg, Ca, Mn Co, Cu and Zn.

In an embodiment according to the present invention the Applicant has improved a method for preparing metal chelates having formula (I), which envisages the direct reaction of MHA and metals (II) oxides such as: Mg, Ca, Mn, Co, Cu, Zn and Fe.

In this new embodiment oxides of metals (II) are used instead of carbonates as described in application PCT/IT99/00225, and technical and operating conditions are unchanged with respect to those referred to in application PCT/IT99/00225, and therefore said operating conditions are regarded as contained in the present application.

Advantageously, the following are used: magnesium oxide mixed with magnesium carbonate or alternatively completely replacing magnesium carbonate, zinc oxide mixed with zinc carbonate or alternatively completely replacing zinc carbonate, and calcium oxide mixed with calcium carbonate or alternatively completely replacing calcium carbonate.

The Applicant has found it advantageous to use for human nutrition the following metal chelates:

$(CH_3SCH_2CH_2CH(OH)COO)_2Zn.2H_2O$

The two water molecules are not bonded to the metal.

$(CH_3SCH_2CH_2CH(OH)COO)_2Cu$

It is an anhydrous complex without water molecules bonded to the metal.

$(CH_3SCH_2CH_2CH(OH)COO)_2Co.2H_2O$

The two water molecules are complexed.

$(CH_3SCH_2CH_2CH(OH)COO)_2Mn.2H_2O$

The two water molecules are complexed.

$(CH_3SCH_2CH_2CH(OH)COO)_2Ca.2H_2O$

The two water molecules are not bonded to the metal.

$(CH_3SCH_2CH_2CH(OH)COO)_2Mg.2H_2O$

The two water molecules are not bonded to the metal.

In another embodiment of the present invention said third aim is achieved by suggesting a method for preparing metal chelates with methionine hydroxy analogue or one of its salts, both in solid form with iron (II), vanadium (IV) and/or vanadium (V) and molybdenum (V) and/or molybdenum (VI), and in liquid form in aqueous solution with iron (II) and (III) and chrome (III).

In the case of vanadium and molybdenum the method for preparing their chelates consists in the reaction of their corresponding oxides with methionine hydroxy analogue.

Alternatively, in the case of vanadium and molybdenum the method for preparing their chelates consists in the reaction of their corresponding metal salts with methionine hydroxy analogue.

For instance, an amount of solid $V_2O_5$ or $MoO_3$ is added with a solution of methionine hydroxy analogue at a high temperature and under stirring. A transparent solution and a solid precipitate of a vanadium or molybdenum chelate are obtained from the reaction.

In a preferred embodiment the Applicant has arranged in a receptacle vanadium oxide $V_2O_5$ and methionine hydroxy analogue MHA. Vanadium oxide and methionine hydroxy analogue are present in a molar ratio of 1:2 to 1:8, preferably 1:4 to 1:6 (Vanadium/MHA).

The receptacle is equipped with stirring means, heating means and means for reaction reflux. The reaction takes placed under mechanical stirring and under reflux for a time between 20 and 60 minutes, preferably 30 minutes. At the end of the reaction a dark green solution is obtained, from which after cooling a solid green precipitate is obtained. From the chemical and physical analysis of the precipitate the Applicant has found confirmation that it is a vanadium (IV) complex having formula $VOL_2$, where L=deprotoned methionine hydroxy analogue.

During the reaction vanadium (V) oxide reduces to vanadium (IV).

In the case of iron (II) the method of preparation takes place by reaction of sodium salt (or an alkali metal or alkaline-earth metal salt) of MHA with ferrous sulfate (or any other soluble iron (II) salt) in water environment.

The molar ratio MHA/Iron (II) is of 2:1 for completing the reaction. Ferrous chelate precipitates from the reaction environment and is filtered and washed with water so as to eliminate soluble sodium sulfate which builds up.

After filtration and washing the chelated product is then dried so as to reduce the amount of absorbed water. The product is a pale yellow powder, little water soluble, having formula:

$(CH_3SCH_2CH_2CH(OH)COO)_2Fe.2H_2O$.

Water molecules are bonded directly to iron (TGA data).

The infrared vibrational spectrum shows the occurred chelation: as a matter of fact, the spectrum has a series of characteristic bands according to the above structure.

In particular, the band due to the asymmetric stretching of carboxylic group can be observed at $1,596\ cm^{-1}$ significantly moved to low frequencies with respect to free MHA ($1,720\ cm^{-1}$) as expected for deprotonation and coordination. A pure and stable product is thus obtained.

In an embodiment of the present invention stable solutions of iron (II) and chrome (III) chelates with MHA can be obtained by dissolution in water environment of soluble salts of iron or chrome (III) and of MHA in a ration MHA/M (III)$\geq$2, preferably 3, and keeping pH at a suitable value so as to prevent precipitation of the corresponding hydroxides.

In a preferred embodiment the Applicant has improved the preparation of a stable solution of chrome (III) in which a chrome salt, for instance chrome sulfate $Cr_2(SO_4)_3$ is reacted with methionine hydroxy analogue MHA under stirring, for instance by heating, for a time between 20 and 120 minutes, preferably between 30 and 60 minutes. Chrome salt and methionine hydroxy analogue are present in a molar ration of 1:2 to 1:30, preferably 1:2 to 1:20. At the end of the reaction a solution of chrome(III) complexes with methionine hydroxy analogue is obtained.

In another preferred embodiment of the present invention said fourth aim is achieved by suggesting the use of said new chelates, both in solid form with iron (II), vanadium (IV) and/or vanadium (V) and molybdenum (V) and/or molybdenum (VI), and in liquid form in aqueous solution with iron (II) and (III) and chrome (III), for the preparation of metal integrators for human and animal nutrition.

Metal chelates described in the present invention can be used mixed one with the other in various quantitative ratios for preparing metal integrators. Therefore, the integrators suggested both for human and animal nutrition can contain one or more metal chelates according to the present invention.

With reference to the metal chelates described above and according to the present invention the Applicant has made a series of experimental tests.

In Vitro Tests

For in vitro tests cells of human colon adenocarcinoma (CACO-2) have been used, these being the most frequently used in vitro system for studies on intestinal functionality, in particular as far as transepithelial transport is concerned, since said cells (CACO-2) develop ultra-structural, functional and electrical properties that are similar to those of small intestine.

The formation of intercellular links can be monitored through measurements of transepithelial electric resistance (TEER) of the single layer of cells. Since intercellular links limit the (para-cellular) movement of solutes, TEER alterations are commonly used as permeability index of said links.

Figure 1:
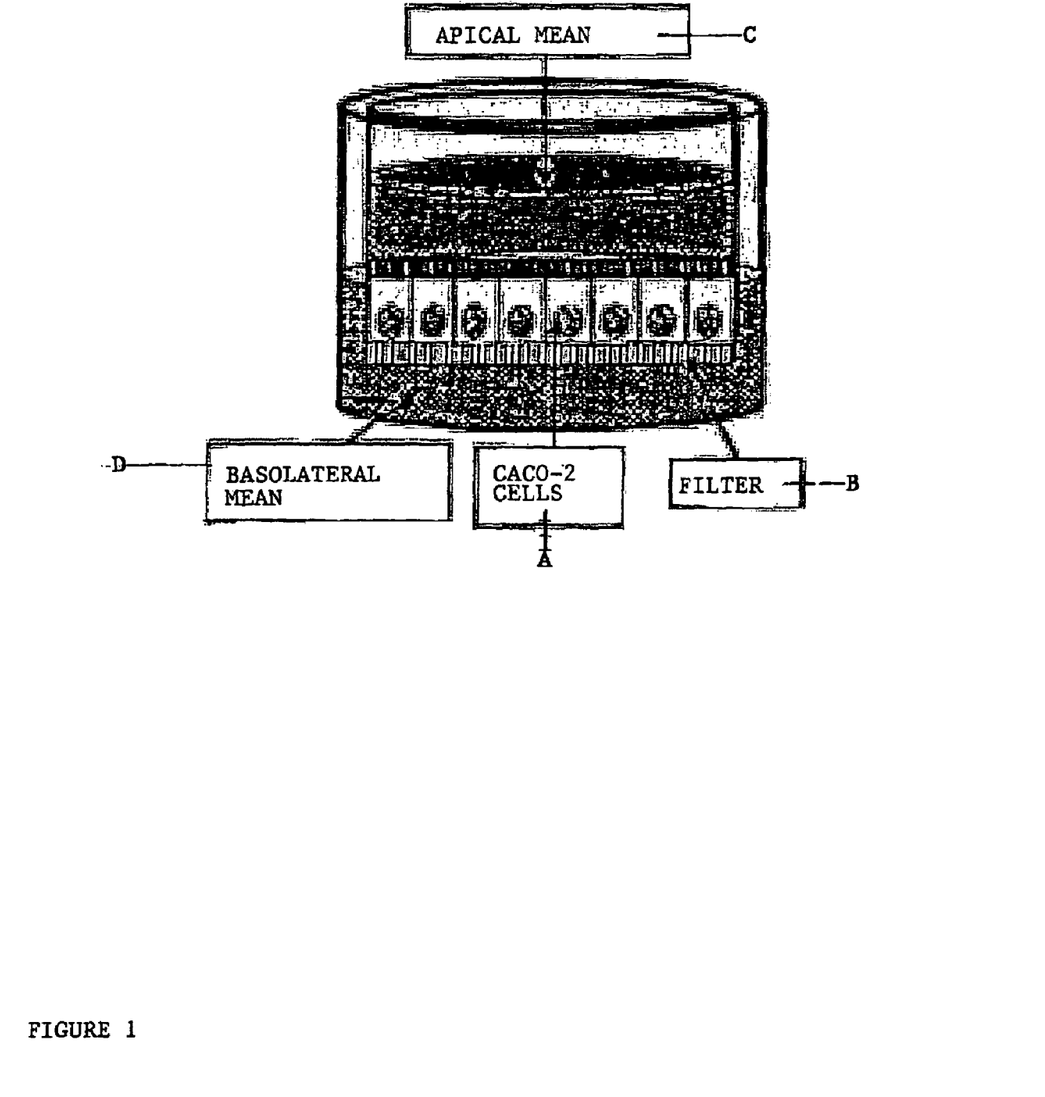

The equipment used for cell growth and differentiation is shown in FIG. 1.

Said cells, referred to with A in FIG. 1, have been grown and differentiated on a carrier (permeable filter), referred to with B in FIG. 1, until a single layer of differentiated cells joined by functional intercellular links is formed. Said filter B separates the apical environment C, (AP), (simulating intestine lumen) from the basolateral environment D, (BL), placed in the lower chamber, simulating capillary blood flow.

Said cells have been treated for 3 hours with two different concentrations of Fe(III)/MHA (1:3) and Fe(III)/NTA (1:2) (nitriltriacetic acid taken as reference chelate), in a buffer solution at pH 5.5 and 37° C. Said solutions have been placed in the apical compartment C (AP), whereas the basolateral compartment D (BL) contained an iron-free solution of apotransferrin placed in a buffer solution at pH 7.4.

Figure 2:
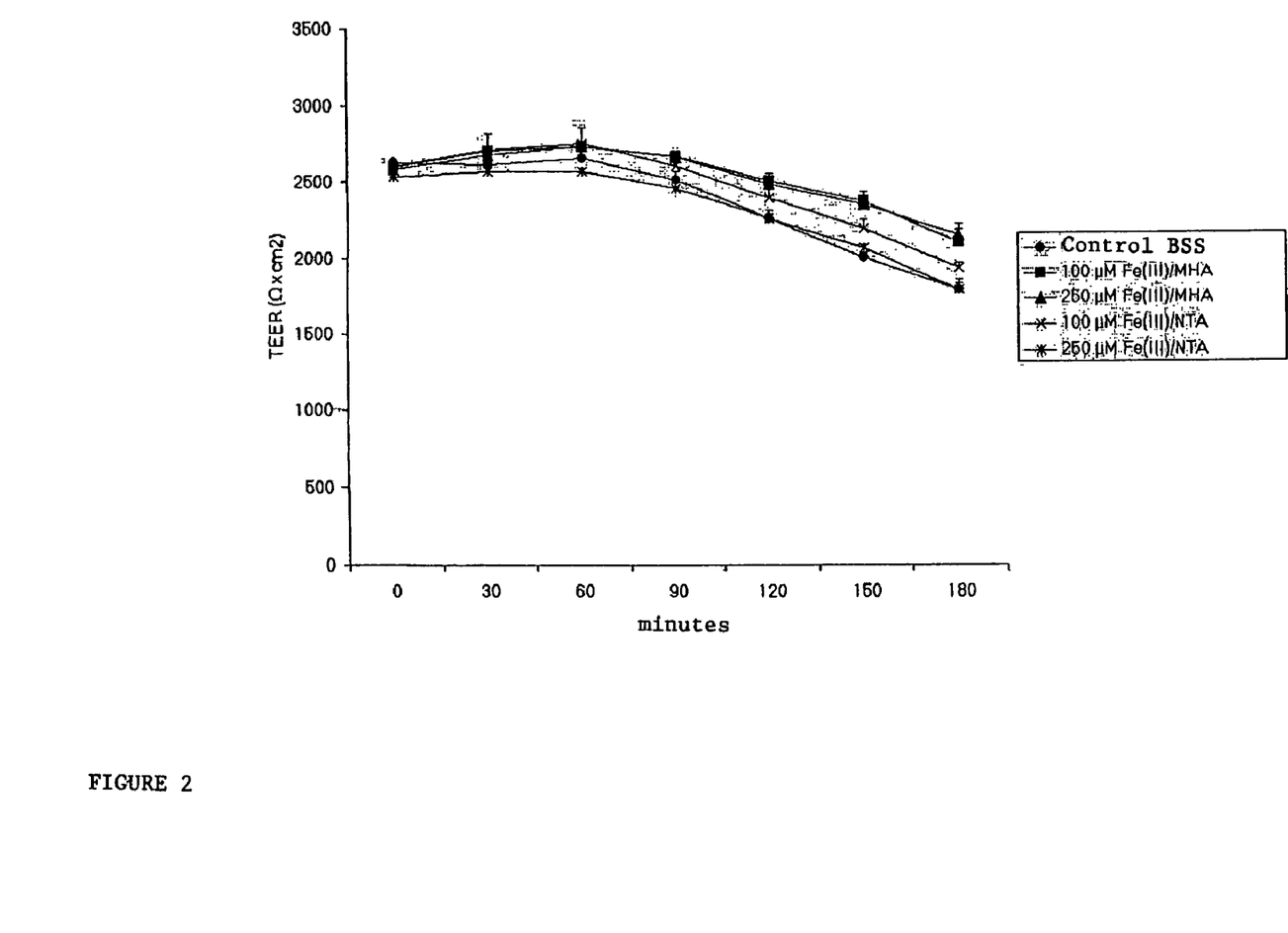

During said experiment, at pre-established time intervals, TEER has been measured in $\Omega \cdot cm^2$. FIG. 2 (every 30 minutes over 3 hours) and FIG. 3 after 24 hours.

Figure 4:
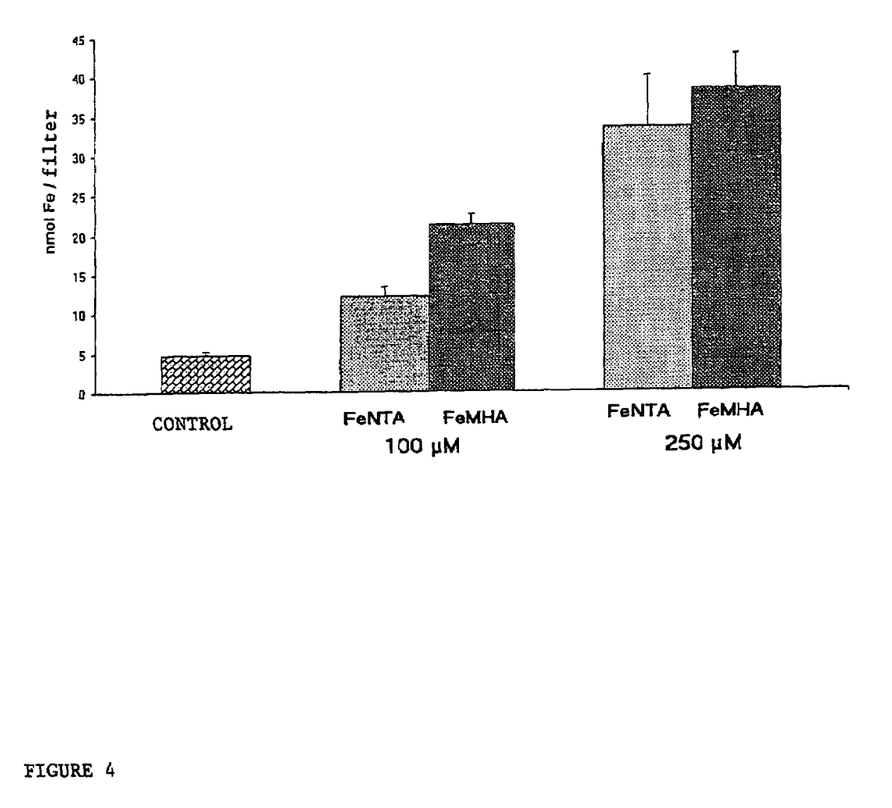

The results are shown in FIG. 4, indicating the content of intracellular iron after 3 hours of treatment with Fe(III)/MHA and Fe(III)/NTA at different concentrations. Data are expressed in nmoles iron/filter.

As can be inferred from FIG. 4, the passage of iron/MHA chelate from the apical environment, C, to the cell is higher than the one observed in the control.

Figure 5:
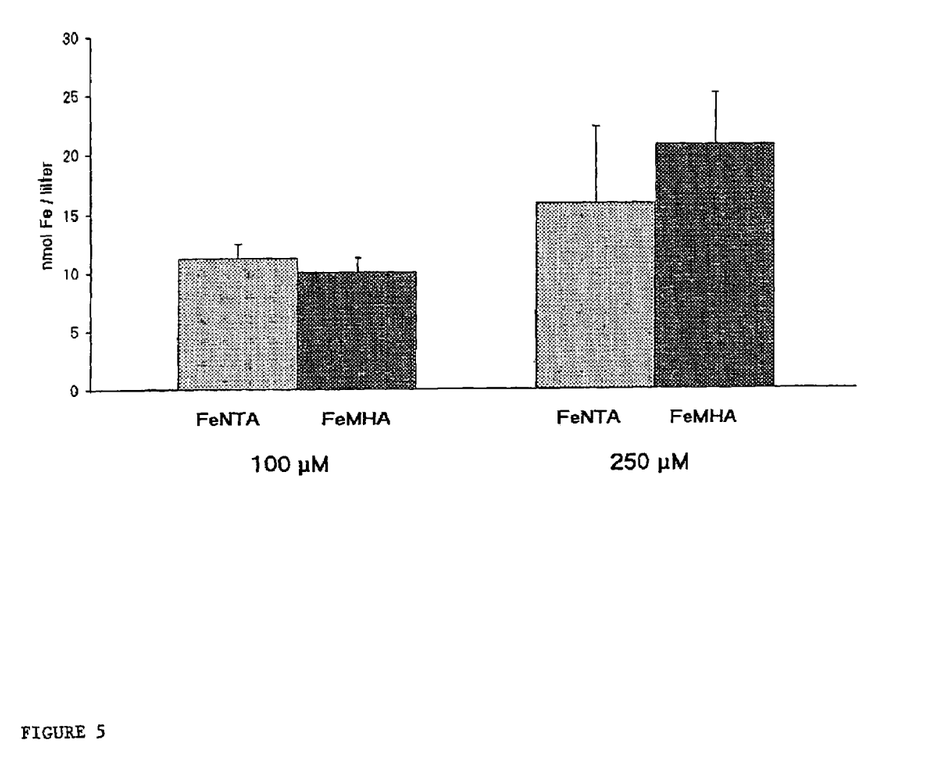

Moreover, from FIG. 5 (showing iron transport from apical environment C to basolateral environment D after treatment with two different concentrations of Fe(III)/MHA and Fe(III)/NTA) it can be inferred that the concentration of transported iron is comparable. Data are expressed in nmoles iron/filter.

Data shown in FIGS. 4 and 5 confirm that iron chelate is strongly absorbed by cells of intestinal microvilli and moves within blood flow.

From FIG. 2 (showing TEER measurements) it can be inferred that intercellular links are unchanged, thus proving the non-toxicity of iron chelate towards cells, contrarily to what happens in the case of unchelated iron such as ferrous sulfate.

Figure 3:
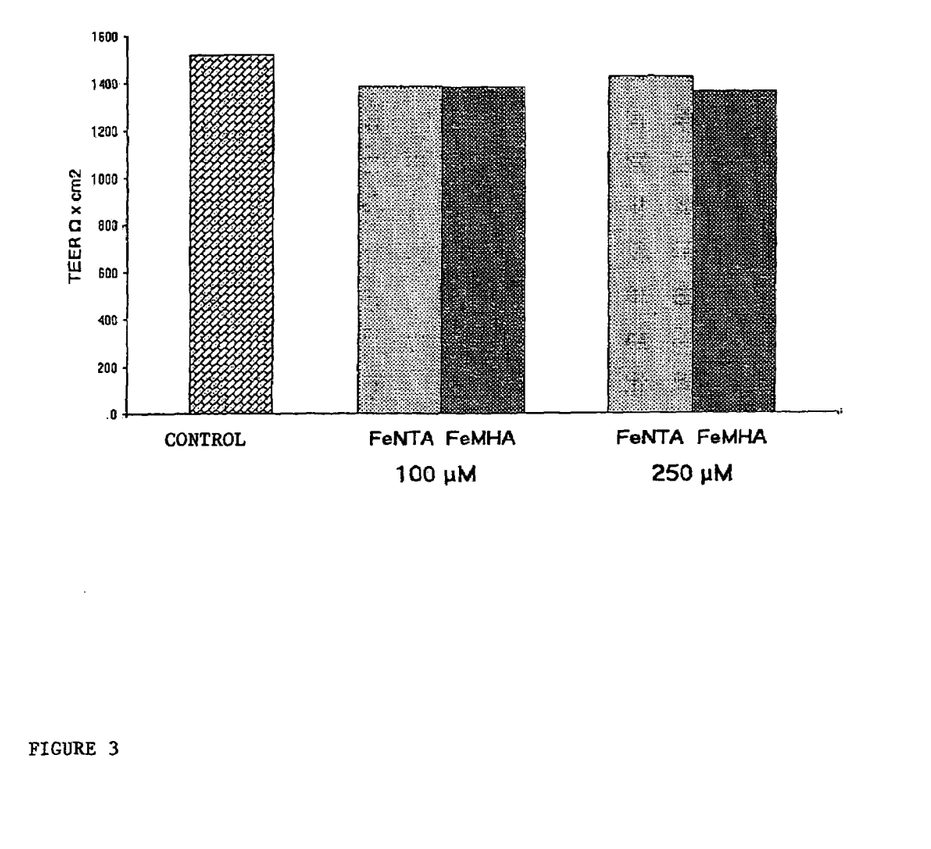

FIG. 3 shows the measurement of TEER 24 hours after the buffer solution at 5.5 containing iron/MHA or iron/NTA has been removed keeping the cells in culture. Said FIG. 3 shows how iron chelate/MHA is stable within cells causing no toxic effect.

Finally, the tests show that MHA/M chelates according to the present invention are efficiently absorbed, stable within intestinal cells and non-toxic.

The results shown above support the use of said new chelates, both in solid form with iron (II), vanadium (IV) and/or vanadium (V) and molybdenum (V) and/or molybdenum (VI), and in liquid form in aqueous solution with iron (II) and (III) and chrome (III), for the preparation of metal integrators for human and animal nutrition.

In Vivo Tests

Said tests have involved both monogastric animals (such as pigs) and polygastric animals (such as calves).

a) Monogastric Animals (Pigs)

Two test groups of pigs (Control and Test) of 35 days of age and weaned at 19 days, were administered a food differing only in the zinc source.

Said food consisted, pro kg of food as such, of 3,500 Kcal ED, 1.15 g of lysine, and a total amount of zinc element of 81 mg (81 ppm), of which 31 mg (31 ppm) were given by raw materials, whereas 50 mg (50 ppm) were respectively in form of zinc sulfate (Control) and zinc chelate with MHA (Test) according to the present invention.

The two groups of animals were balanced by nest, living weight and sex and were fed for 27 days. Other 4 animals were immediately sacrificed and a sampling was made of them according to the following procedure. The two groups of animals were weighed before starting the test and after 27 days. At the end of the test the pigs were sacrificed and stomach, intestine, left kidney and liver were removed from every pig. Stomach and intestine were emptied and weighed again so as to obtain the net weight of said organs. A sample of kidney, liver and brain was taken and frozen. Stomach, intestine, left kidney and liver were then put together with the remaining carcass and homogenized with a mixer. A sample was then taken from the mass thus obtained and frozen. The samples were then dehydrated with a dehydrating device and underwent chemical analysis.

The level of zinc, copper and iron were determined on the lyophilized samples by atomic absorption spectroscopy. The body levels of zinc were referred to the product.

On the basis of the body's "net" weight (i.e. without the content of the digestive tube) and of its content of zinc at test beginning and end it was possible to determine also daily zinc retention. The results of the chemical analyses carried out on the samples are shown in Table 1. The pigs were sacrificed at an average weight of 16.2 kg. The average daily weight increase was of 324 g.

As can be inferred from the data shown in Table 2 concerning daily zinc retention of the two different sources, the integration of zinc chelate was retained by the organism 26% more (P=0.07) than the integration with zinc sulfate. Table 3 shows the data concerning the effect of the zinc source on the content of zinc, copper and iron in liver, kidney and brain and, therefore, on the interaction with said elements present in the diet under inorganic form. As a matter of fact, it is known about the interaction exerted by said free ions by reducing one the absorption of the other.

The content of said three minerals in liver was not affected by the diet and therefore by the zinc source. Average values were 296 mg/kg for zinc, 63 mg/kg for copper and 220 for iron. Conversely, kidney showed a higher content of zinc (+18%, P=0.07), of iron (+36%, P=0.01) and of copper (+36%, P=0.12), and did not reach only for the latter value the threshold of statistic significance, though it showed a tendency towards an increase in the retention of said metal element.

In brain there was a tendency towards a higher content of zinc (+13%), of copper (+20%), of iron (+25%).

The obtained results point out a higher bioavailability of the metal element in chelated form with respect to inorganic sources such as sulfates, and further a lower interaction with other ions, which results in a higher retention of the latter.

As is known, pigs are one of man-closest animal models and as such they are often used as model for evaluations and studies in the human field.

b) Polygastric Animals (Meat Cattle)

Two groups of female Charolaise calves (30 months old) comprising 6 animals each, with an average starting weight of 567 kg (Control and of 565 kg (Test), were fed for 90 days with the same diet. The only difference was that the Control group was administered zinc carbonate and the Test group zinc chelate according to the present invention. Daily ingestion was of 22 kg/animal and the total daily supply of zinc element was of 700 mg.

Living weight at test beginning and end, dead weight and slaughtering yield were determined for each animal. Data are shown in Table 4.

Animals fed with zinc chelate with respect to those fed with zinc carbonate have a significantly higher final weight (652 kg vs. 642 kg, p<0.05), a significantly higher daily weight increase (1,039 g vs. 934 g, p<0.05), a significantly higher carcass weight (377 kg vs. 366 kg, P<0.01), and a significantly higher yield (57.83% vs. 57.03%, p<0.01). Data are shown in Table 4. The effect due to the presence of zinc chelate in the ratio administered to animals is shown in Table 5.

Said results show an evident improvement of the aforesaid zootechnical performances of zinc chelate with respect to inorganic sources of said element.

Stability constants for the various Fe/MHA complexes have been calculated with potentiometric titrations. The stability of iron (III) complexes is very high and chelated species form also at acid pH. Uncomplexed $Fe^{3+}$ ions are present only at very low pH values (<2.5), whereas at higher pH values all iron (III) is complexed as chelated species metal/ligand=1:2.

TABLE NO. 1

|  |  | Chelate | Sulfate | E.M.S. |
|---|---|---|---|---|
| Number of days | n | 26.3 | 26.4 |  |
| Initial living weight | kg | 7.54 | 7.33 | 0.50 |
| Final living weight | kg | 16.14 | 16.20 | 0.55 |
| Daily increase | g | 327 | 321 | 11 |
| Diet | g | 544 | 548 | 1.9 |
| Conversion index |  | 1.68 | 1.72 | 0.054 |
| Initial net living weight | kg | 7.31 | 7.49 | 0.48 |
| Final net weight | kg | 15.57 | 15.76 | 0.55 |
| Daily net increase | g | 314 | 313 | 11 |

TABLE NO. 2

|  |  | Chelate | Sulfate | E.M.S. |
|---|---|---|---|---|
| Daily Zn retention | mg | 5.40 | 5.27 | 0.37 |

TABLE NO. 3

|  | Chelate | Sulfate | E.M.S. | Statistic significance |
|---|---|---|---|---|
| Liver |  |  |  |  |
| Zinc | 292 | 300 | 21 | P = 0.80 |
| Copper | 63.6 | 62.5 | 6.3 | P = 0.91 |
| Iron | 240 | 199 | 35 | P = 0.44 |

TABLE NO. 3-continued

|  | Chelate | Sulfate | E.M.S. | Statistic significance |
|---|---|---|---|---|
| Kidney |  |  |  |  |
| Zinc | 97.5 | 82.3 | 5.5 | P = 0.07 |
| Copper | 55.0 | 40.2 | 6.4 | P = 0.12 |
| Iron | 244 | 179 | 11.8 | P < 0.01 |
| Brain |  |  |  |  |
| Zinc | 53.9 | 47.6 | 3.5 | P = 0.23 |
| Copper | 28.1 | 23.3 | 3.5 | P = 0.35 |
| Iron | 100.9 | 80.6 | 9.9 | P = 0.17 |

TABLE NO. 4

| Diet | Initial weight | E.M.S. |
|---|---|---|
| Control | 567.700000 | 31.845747 |
| Zn | 565.633333 | 31.845747 |

|  | Final weight | E.M.S. |
|---|---|---|
| Control | 642. | 2.694781 |
| Zn | 652. | 2.691923 |

Control vs. Zn P < 0.05

| Diet | Daily increase | E.M.S. |
|---|---|---|
| Co | 931. | 29.94201 |
| Zn | 1,039. | 29.91025 |

Control vs. Zn P < 0.05

| Diet | Carcass weight | E.M.S. |
|---|---|---|
| Control | 366. | 1.812368 |
| Zn | 377. | 1.810445 |

Control vs. Zn P < 0.01

| Diet | Slaughtering weight | E.M.S. |
|---|---|---|
| Control | 57.03 | 0.1132212 |
| Zn | 57.85 | 0.1131011 |

Control vs. Zn P < 0.01

TABLE NO. 5

|  | Calf number | Initial weight kg | Final weight kg | Daily increase g | Total increase kg | Dead weight kg | Slaughtering weight kg |
|---|---|---|---|---|---|---|---|
| CONTROL | 1 | 583.5 | 670.75 | 1,050 | 94.50 | 383 | 0.578 |
|  | 2 | 583.5 | 670.75 | 970 | 87.30 | 383 | 0.571 |
|  | 3 | 599.5 | 675.96 | 850 | 76.50 | 388 | 0.574 |
|  | 4 | 540.9 | 623.67 | 920 | 82.80 | 353 | 0.566 |
|  | 5 | 568.1 | 649.12 | 900 | 81.00 | 370 | 0.570 |
|  | 6 | 532.3 | 624.13 | 1,020 | 91.80 | 357 | 0.572 |

TABLE NO. 5-continued

|  | Calf number | Initial weight kg | Final weight kg | Daily increase g | Total increase kg | Dead weight kg | Slaughtering weight kg |
|---|---|---|---|---|---|---|---|
| TEST | 1 | 625.6 | 724.61 | 1,100 | 99.0 | 421 | 0.581 |
|  | 2 | 676.8 | 789.29 | 1,250 | 112.5 | 457 | 0.579 |
|  | 3 | 582.7 | 686.21 | 1,150 | 103.5 | 398 | 0.580 |
|  | 4 | 564.0 | 653.98 | 1,000 | 90.00 | 378 | 0.578 |
|  | 5 | 476.5 | 557.49 | 900 | 81.00 | 320 | 0.574 |
|  | 6 | 468.2 | 548.28 | 890 | 80.10 | 318 | 0.580 |

What is claimed is:

1. A method for preparing a metal chelate selected from the metal chelate of general formula (I):

$$(CH_3SCH_2CH_2CH(OH)COO)_2M.nH_2O \qquad (I)$$

wherein:
M is a bivalent metal cation selected from the group consisting of: Mg, Ca, Mn, Co, Cu, Zn and Fe, and n is between 0 and 6,
said method comprising a step in which there is a direct reaction between a metal (II) oxide of M and $CH_3SCH_2CH_2CH(OH)COOH$ and/or salts thereof.

2. The method according to claim 1, wherein the metal chelate is selected from the group consisting of:
$(CH_3SCH_2CH_2CH(OH)COO)_2Zn.2H_2O$;
$(CH_3SCH_2CH_2CH(OH)COO)_2Cu$;
$(CH_3SCH_2CH_2CH(OH)COO)_2Co.2H_2O$;
$(CH_3SCH_2CH_2CH(OH)COO)_2Mn.2H_2O$;
$(CH_3SCH_2CH_2CH(OH)COO)_2Ca.2H_2O$;
$(CH_3SCH_2CH_2CH(OH)COO)_2Mg.2H_2O$; and
$(CH_3SCH_2CH_2CH(OH)COO)_2Fe.2H_2O$.

3. A method for preparing a metal chelate of formula $(CH_3SCH_2CH_2CH(OH)COO)_2Fe.2H_2O$ comprising a step in which there is a direct reaction between an alkali metal or alkaline-earth metal salt of methionine hydroxy analogue and a soluble iron (II) salt in water.

4. The method according to claim 3, wherein said alkali metal salt is a sodium salt of methionine hydroxy analogue and said soluble iron (II) salt is a ferrous sulfate.

5. The method according to claim 4, wherein said iron (II) chelate obtained from the reaction is filtered and washed with water.

* * * * *